United States Patent [19]

Mioduszewski et al.

[11] Patent Number: 5,723,504
[45] Date of Patent: Mar. 3, 1998

[54] AMADORI REACTION COMPOUNDS AND PRODUCTS, PROCESS FOR THEIR MANUFACTURE, AND THEIR USE AS CYTOKINE INDUCERS

[75] Inventors: Jan Zbigniew Mioduszewski, Warsaw; Krystyna Witkiewicz; Anna Inglot, both of Wroclaw, all of Poland

[73] Assignee: Torf Establishment, Liechtenstein

[21] Appl. No.: 284,635

[22] PCT Filed: Feb. 11, 1993

[86] PCT No.: PCT/EP93/00327

§ 371 Date: Oct. 24, 1994

§ 102(e) Date: Oct. 24, 1994

[87] PCT Pub. No.: WO93/16087

PCT Pub. Date: Aug. 19, 1993

[30] Foreign Application Priority Data

Feb. 13, 1992 [PL] Poland ........................ 293464
Mar. 3, 1992 [EP] European Pat. Off. ........ 92103614

[51] Int. Cl.$^6$ .................. A61K 31/73; A61K 39/39; A61K 9/00; C12P 21/00
[52] U.S. Cl. .................. 514/885; 514/2; 514/23; 514/42; 536/17.2; 536/17.4; 536/18.7; 536/123.1; 536/123.13; 530/300
[58] Field of Search .................. 536/17.4, 17.2, 536/123.1, 123.13, 18.7; 514/42, 2, 23, 885; 530/300

[56] References Cited

U.S. PATENT DOCUMENTS 4,022,920  5/1977  Doornbus et al. .................. 426/533

FOREIGN PATENT DOCUMENTS 0152856  8/1985  European Pat. Off. .
0111211  5/1986  European Pat. Off. .
3601472  7/1987  Germany .
WO 89/09786  10/1989  WIPO .
9216216  10/1992  WIPO .

OTHER PUBLICATIONS

Analysis of the 220–MHz, P.M.R. spectra of some products of the Amadori and Heyns rearrangements Altena H. J. et al. Carbohydrate Research, vol. 92, 1981, pp. 37–49.

Glycoproteins–Their Composition, Structure and Function–Part A Alfred Gottschalk, B.B.A. Library, vol. 5, 1972 pp. 146–157.

Quantitative Untersuchungen der Reaktion von Hexosen mit Aminsauren Heyns K. et al. Justus Liebigs Annalen der Chemie, vol. 703, 1967, pp. 202–214.

Gottschalk, Alfred, B.B.A. Library vol. 5, Part A, Glycoproteins, Elsevier Publishing Co., New York, 1972, pp. 141–156.

Primary Examiner—Gary L. Kunz
Attorney, Agent, or Firm—Ostrolenk, Faber, Gerb & Soffen, LLP

[57] ABSTRACT

Novel Amadori reaction compounds have the formula $R_1$—NH—$R_2$, wherein $R_1$ comprises the D-form of a 1-amino-1-deoxy-2-ketose radical derived from a sugar radical selected from the group of glucose, xylose, galactose, rhamnose, fructose, mannose, 6-deoxyglucose, glucosamine and galactosamine, and $R_2$ comprises the L-form of an aminoacid or peptide radical selected from the group of serine, glycine, proline, histidine, arginine, alanine, aspartic acid, glutamic acid, phenylalanine, treonine, cysteine, cystine, glutamine, asparagine, methionine, tyrosine, hydroxyproline, tryptophane, valine isoleucine, lysine and leucine. Compounds and combinations of compounds having the general formula $R_1'$—NH—$R_2'$, wherein $R_1'$ comprises a 1-amino-1-deoxy-2-ketose radical derived from the group of simple sugars, oligo- and polysaccharides, and $R_2'$ comprises an aminoacid or a peptide radical, are used to produce pharmaceutical preparations which in contact with human leukocytes produce interferon and other cytokines.

49 Claims, No Drawings

AMADORI REACTION COMPOUNDS AND PRODUCTS, PROCESS FOR THEIR MANUFACTURE, AND THEIR USE AS CYTOKINE INDUCERS

This application was filed under 35 USC 371 as a national stage of International case PCT/EP93/00327 filed Feb. 11, 1993.

BACKGROUND OF THE INVENTION

1. Field of the Invention

The present invention related to novel Amadori reaction compounds and products, to the production thereof and to a new use of these compounds and products, having at least partly entered an Amadori rearrangement as per the following reaction scheme and/or a Maillard reaction:

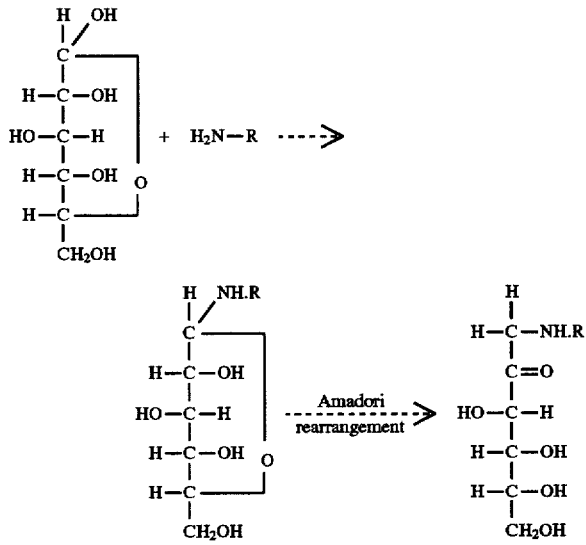

Amadori reaction products are known; they are reaction products, for example, of an aminoacid or a peptide with a sugar, oligo- or polysaccharide having entered an Amadori rearrangement (J. Biol. Soc. 215 (1955), Henri Borsock et al.). Thus, in DE-C-3914354, a water-soluble glycoprotein of an aminoacid and a sugar is described which is isolated from an extract of Avena sativa seeds. Further, EP-A-406087 describes water-soluble polysaccharide-glycopeptide complexes which are derived from the cell wall of Gram positive bacterium, and J. Biol. Chem. 1985, 260/9 states that NMR-spectroscopy has been used to characterize Amadori reaction products formed by reaction of glucose with free amino groups of protein.

2. Description of the Related Art

The invention now describes specific novel Amadori rearrangement compounds.

These compounds reduce potassium ferricyanide, a test reaction for biological active substances formed in a reaction of sugar and aminoacid.

The invention further relates to a novel use of such compounds and simultaneously a novel use of Amadori reaction products of sugars and aminoacids in general. In the past, nobody has tested the various steps of purification of the extract of an Amadori reaction product (in order to get ride of ballast substances and impurities) for biological activity.

Immunostimulating drugs are indeed known from natural sources such as mistletoe extracts, peat extracts etc. with the drawback of expensive treatment of large quantities of raw material to obtain a few grams of active substance. Uncontrolable impurities might lead to toxicity and side effects and therefore, further, to problems with administration during practical use due to the complex nature and the hardly reproducible composition.

Comparable products or product mixes from artificial sources, such as interferon or other genetic engineering methods are even more expensive to make furthermore, the molecules of human interferon are very often too big to penetrate the human cell wall so that only a fraction of the administered dose is effectively becoming active. Also, genetic engineering products usually have side effects and some are even toxic furthermore, some of them act effectively on one day and not on the next day, for reasons unknown so far.

Surprisingly, it has now been found that nearly any simple amino-acid/sugar complex after having at least partly entered an Amadori rearrangement does not show any of the above-mentioned disadvantages but on the contrary has a surprisingly high immuno-logical activity. They can therefore be used in pharmaceutical formulations and in cosmetics. These small molecules easily penetrate the cell wall and virtually act as a nutrient. They induce the formation of natural interferon and other cytokines, including tumor necrosis factor. Even three days after the administration, they still show this stimulating effect on biological activity. This effect increases with increasing completion of the Amadori rearrangement and decreases again with increasing decomposition of the complex.

Instead of simple sugars also—preferably low molecular weight, especially of less than 1000 daltons—polysaccharides may be used, for instance dextran, which react similarly. Polysaccharides show biological activity and may retain some of this activity after they become oligosaccharides.

Very little has been known heretofore about the biological activity of these compounds. It was now found that combinations of these substances in contact with human leukocytes produce interferon and other cytokines. This is called polyclonal activation of the cells.

It is possible to rest the substances produced under the influence of these compounds and to determine the biological activities in international units relevant to specific cytokines. These compounds are of especially high biological activity within a range of pure substance concentrations from 1–100 µg/ml. Within the molecule, the specific nature of the aminoacid is more important than the nature of the sugar part of the molecule.

Reaction products of L-aspartic acid with glucose or galactose—after having gone through the Amadori rearrangement—when contacted with human leukocytes and incubated in tissue culture mediate at 37° C. for 20 hours in an atmosphere of 5% $CO_2$ will produce from 30–1000 antiviral units of interferon. The interferon is measured in a bioassay using human cancer cells. Under the influence of these compounds, tumor necrosis compounds may also be produced.

The products which allow such an unexpected use have the general formula

wherein $R_1'$ represents a 1-amino-1-deoxy-2-ketose radical derived from the group of simple sugars, oligo- and—preferably low molecular weight, especially of less than 1000 daltons—polysaccharides, and $R_2'$ represents an aminoacid or a —preferably low molecular weight, especially of less than 1000 daltons—peptide radical.

Thus the group of biologically active compounds may cover either the specific Amadori rearrangement compounds described above or the N-substituted derivatives of a number of different aminoacid compounds and one simple sugar, oligo- or —preferably low molecular weight, especially of less than 100 daltons—polysaccharide, or N-substituted derivatives of one aminoacid compound and a number of simple sugars, oligo- and/or such polysaccharides, or else any combination of such derivatives, every single one of them having sufficient biological activity.

Preferably, $R_1'$ in the above formula may be a radical selected from the D-form of simple sugars, especially (but not exclusively) from the D-form of glucose, xylose, galactose, rhamnose, fructose, mannose, 6-deoxyglucose, glucosamine and galactosamine; $R_2'$ may be a radical selected from the L-form of aminoacid compounds such as serine, glycine, histidine, arginine, glutamine, asparagine, alanine, aspartic acid, glutamic acid, phenylalanine, treonine, cysteine, cystine, methionine, hydroxyproline, tryptophane, proline, tyrosine, valine, isoleucine, leucine and lysine or else peptides of these aminoacids in any combination.

The invention further relates to a process for obtaining the above mentioned compounds and products and whereby an intermediate is formed of the formula

wherein

R' is a 1-deoxy-2-Ketase radical in a straight carbon chain or any O-bridged form of a simple sugar or an oligo- or polysaccharide, and R" represents an aminoacid or a peptide radical, said intermediate being at least partly subjected to an Amadori rearrangement and/or to the Maillard reaction by continued heating of the reaction mixture—preferably under pressure—and simultaneously or subsequently removing the solvents.

In some cases, especially when an aminoacid having two carboxyl groups is used, it is advantageous to add to the process a buffer salt, such as sodium bicarbonate, preferably in a molar ratio of 1:1.

It was further found that the amadori rearrangement products are relatively susceptible to decomposition, and that decomposition products have the nature of dark brown and tar-like, unidentified compounds having lost their biological activity. Therefore it is preferred to stop the Amadori rearrangement reaction at a stage at which the reaction mixture becomes light orange-brown in color.

It is interesting to note that the intermediate reaction products, formed when the originally opaque solution of the aminoacid becomes clear (before the Amadori rearrangement), are easily hydrolyzed, i.e. the reaction is reversible. With increasing rearrangement, the reversibility diminishes, i.e. the products become more stable, and the color gradually changes from light yellow to light orange, and then finally to orange-brown when the Amadori rearrangement seems to be complete. Samples taken during such rearrangement reaction and tested (according to various procedures described later) proved that the biological activity increases with the Amadori reaction progressing, and decreases when further heating results in decomposition, for which a color change to dark brown is a sign. Immediate reduction of ferricyanide and the resulting color change will occur if the reaction mixture contains other keto groups and/or sulfur containing aminoacids such as cysteine; otherwise it will occur within 3 to 5 min, which is a good check for the degree of Amadori rearrangement developed. Unreacted sugars would show the color change after half an hour or several hours only.

Isolation of the pure Amadori rearrangement products is carried out according to known methods based on binding the mixture on a strong cation-exchanger (such as Amberlite® or Dowex®, successively eluting with ammonia water, evaporating a chosen defined fraction of the eluate under reduced pressure and crystallising the pure compound from anhydrous methanol (J. E. Hodge and B. E. Fisher, Methods in Carbohydrate Chemistry, Vol. II, Reactions of Carbohydrates, Academic Press, N.Y., London, 1963, page 105–106; or Borsook et al. as quoted earlier; or J. Dubourg and P. Devilliers).

In the process according to the present invention, all the above-mentioned preferences regarding the kind of radicals derived from simple sugar and aminoacid compounds remain unchanged. Additionally, a preferred mixture of sugar substrates comprises the D-forms of glucose, xylose, galactose, rhamnose and fructose in a weight ratio of about 20:10:4:1:1, while the preferred mixture of aminoacid substrates comprises the L-forms of serine, glycine, histidine, arginine, alanine, proline, tyrosine, valine, leucine, isoleucine and lysine in a weight ratio of 20.5:35.8:35.8:132:180:360:216:160:72:68:780.

As already mentioned, the Amadori rearrangement products are able to reduce potassium ferricyanide, such a chemical test reaction provides a basis for quick determination of the biological activity of the composition formed in a reaction of sugar and aminoacid.

It has been found that Amadori reaction products are especially active if a mixture of simple sugars of the same composition and in the same weight ratio as occurring in natural peat extracts are reacted with a mixture of aminoacid compounds of the same composition and in the same weight ratio as occurring in natural peat extracts in the presence of an aqueous solvent, preferably adding a lower alcohol—and optionally inorganic trace elements occurring in such natural peat extracts—at elevated temperature (and optionally under pressure), and subsequently prolonging the heating in order to cause an Amadori rearrangement of the obtained products, simultaneously or subsequently expelling the solvents, stopping the rearrangement reaction at the point when the reaction mixture becomes light orange-brown in color, drying the products thus obtained and purifying the same by means of column chromatography and collecting the fractions that cause maximum reduction of potassium ferricyanide.

In one embodiment, the instant pharmaceutical formulations contain as an active ingredient at least one reaction product of the formula $R_1'$—NH—$R_2'$ or a specific compound of the formula $R_1$—NH—$R_2$ together with a pharmaceutically acceptable carrier and/or an adjuvant and/or optionally a lubricant in a weight ratio of active ingredient to the remaining components of between 1:1 and 1:100, preferably 1:8 to 1:20 and most preferably about 1:9.

Another advantageous pharmaceutical formulation contains—in addition to the active ingredient—lactose and a lubricant; the weight ratio of lactose to the lubricant being between 20:1 and 100:1, preferably 50:1.

These pharmaceutical preparations are used to treat and/or prevent hematological and/or immunological diseases, and/or stimulate the immunosystem of humans and/or mammals by the induction of cytokine formation.

Another use for the active ingredients is in cosmetic preparations. The active ingredient is present in such preparations in amounts of 0.01–10% by weight, preferably 0.01–1% by weight and especially in amounts of 0.05–0.1%. These cosmetic preparations contain—besides the active ingredient—usual carriers, adjuvants, enriching components and/or fragrants.

DETAILED DESCRIPTION OF THE PREFERRED EMBODIMENTS

The present invention will be further explained and demonstrated in the following examples, which do not limit in any respect the scope of the present invention.

EXAMPLE 1

A 25 ml flask of a rotary evaporator placed in a heated water bath was charged with:

1.47 g (0.01M) L-glutamic acid
0.84 g (0.01M) $NaHCO_3$
0.91 g D-glucose
0.91 g glactose and
3.00 ml of redistilled water The mixture was heated up to 80° C. whereby—preferably under reduced pressure—50% of the water was evaporated and then—under atmospheric pressure—heated to a temperature of 80°–85° C., at which it was kept for 120 min until it became orange in color. The syrup-like concentrated aqueous solution was then evaporated to dryness under reduced pressure. The orange-red solid reaction product thus obtained was marked with the symbol D-10 and saved for biological tests.

EXAMPLE 2

A 25 ml flask of a rotary evaporator placed in a heated water bath was charged with:

1.33 g (0.01M) L-aspartic acid
0.84 g (0.01M) $NaHCO_3$
0.91 g of D-glucose
0.91 g of galactose and
3.00 ml of redistilled water The mixture was heated up to 80° C. with stirring (by means of rotation), concentrated under pressure, whereby a total volume of 1.5 ml water was vaporized, and then treated under atmospheric pressure at a temperature of 80°–85° C. until it became light orange in color; this took place within approx. 60 min.

The reaction mixture was a syrup-like concentrated aqueous solution and was dried under reduced pressure. The resulting reaction product was a dry, yellow-orange powder. It was marked with the symbol D-11 and saved for biological tests.

EXAMPLE 3

A 25 ml flask of a rotary evaporator placed in a heated water bath we charged with:

1.05 g (0.01M) L-serine
0.91 g D-glucose
0.91 g galactose and
2.50 ml redistilled water The mixture was heated to 85°–92° C. with stirring (by means of rotation). After 100 min, the solution became orange in color. The pressure was reduced and the mixture was evaporated to dryness. The reaction product on the walls of the flask formed an orange transparent layer. The reaction product was scraped off and powdered. It was marked with the symbol D-12 and saved for biological tests.

EXAMPLE 4

A 25 ml flask of a rotary evaporator placed in a heated waterbath was charged with:

0.66 g (0.005M) of D-aspartic acid
0.42 g (0.005M) of $NaHCO_3$
0.45 g of D-glucose
0.45 g of galactose and
3.00 ml of redistilled water The mixture was heated up to 80° C., evaporated—under pressure—whereby a volume of 1.5 ml water was vaporized, and then treated—under atmospheric pressure—at a temperature of 85° C. After 60 min. heating the mixture became orange in color; the pressure was reduced and the resulting syrup-like concentrated aqueous solution evaporated to dryness. Before the residue became definitely dry, two times 10 ml water-free ethanol were introduced into the flask and evaporated in order to eliminate residual moisture. The dry reaction product thus obtained was powdered, marked with the symbol D-13 and saved for biological tests.

EXAMPLE 5

In order to obtain—in a synthetic way—an equivalent of the biologically active fraction of a certain natural peat extract, the flask of the rotary evaporator placed in the heated water bath was charged with:

20.5 mg L-serine
35.8 mg L-glycine
35.8 mg L-histidine
132.0 ; mg L-arginine
180.0 mg L-alanine
360.0 mg L-proline
216.0 mg L-tyrosine
160.0 mg L-valine
68.0 mg L-isoleucine
72.0 mg L-leucine
780.0 mg L-lysine
2000.0 mg D-glucose
1000.0 mg D-xylose
400.0 mg D-galactose
100.0 mg D-rhamnose
100.0 mg D-fructose
6.0 ml redistilled water The mixture was stirred by means of rotation and heated under pressure for 45 min at a temperature rising from 75° C. to 86° C. During that period, approx. 3 ml of water were evaporated and the substrates were totally dissolved. The mixture was then treated for 30 min under atmospheric pressure at a temperature of 85°–86° C. for an Amadori rearrangement. During that period the solution quickly became red-brown in color. The pressure was reduced, and heating at 84° C. was continued, thus simultaneously evaporating the solvents. At the end of evaporation, two times 15 ml water-free ethanol were introduced and the reaction mixture was brought to dryness. The flask with the dried reaction product was placed in a desiccator over calcium chloride for 18 hours; then the reaction product was powdered. Approx. 4.5 g of a powdered product were obtained and marked with the symbol $EK_2$-S.

A portion of 4 g of this reaction product was dissolved in 20 ml of distilled water and placed on a chromatographic column of 25 mm×330 mm size, filled with a sorbent Amerlite ® XAD-2 analytical grade. The column was eluted with 0.4 ml/min distilled water. Fractions of 10 ml volume were collected to a total volume of 450 ml. The content of the fractions was monitored chromatographically. Fractions of consecutive numbers 11–13 were combined and evaporated under reduced pressure. These fractions were characterised by a high content of Amadori rearrangement products (confirmed with the potassium ferricyanide reduction test). The product was saved for biological tests under the symbol of $EK_2$-S-11.

Biological tests for determining the biological activity were carried out with immunised Balb/C mice of both sexes, at the age of 8–10 weeks. Immunization of mice is achieved by peritoneal administration of 0.2 ml of a 10% suspension of sheep erythrocytes (SRBC), i.e. of $6\times10^8$ cells. The erythrocytes are fixed in a sterile Alsever's solution of the following composition:

| | |
|---|---|
| glucose | 2.05 g |
| sodium citrate | 0.8 g |
| sodium chloride | 0.42 g |
| citric acid | 0.055 g |
| redistilled water to | 100 ml |

Into such Alsever's solution, a sheep blood cell aseptic sample is introduced in a ratio of 1:1 and the mixture is kept for at least 3 days at +4° C. The thus stabilised erythrocytes are then sampled aseptically and introduced into a phosphate buffered salt solution (PBS) in order to wash them out. Erythrocytes are rinsed with PBS twice, and are centrifugated for 10 min at 2000 rpm. The washed out cells are used in the form of a 10% suspension in PBS. Such a suspension is used for the immunization of Balb/C mice.

The reaction product to be tested was administered intraperitoneally (i.p.) or orally (p.o.) four times at chosen doses, the first administration taking place 2 hours before immunization of the mouse with SRBC, while the remaining three dosages were administered after immunization at 24 h intervals.

Each test group of animals was treated with different doses of the tested reaction product: 10 mg/kg, 1 mg/kg, 0.1 mg/kg and 0.01 mg/kg. A control group of animals was also immunized with SRBC, but instead of the substance to be tested, 0.2 ml of PBS were administered at the same time intervals.

Each group of animals, control and tested groups, in all experiments consisted of 8–12 mice.

On the fourth or (in case of determination of antibodies type 7S) tenth day after immunization, mice were slightly anesthetized with ether and exsanguinated by eyeball extirpation. The blood was collected into test tubes. Next, the spinal cord was broken and spleen removed. The blood was used for obtaining the serum needed for determination of hemagglutinating antibodies of the 19S+7S and 7S types, while spleens were used to prepare the cells useful for determination of the percentage of cells able to form E-rosettes and of hemolytic activity. For such uses, mouse spleens were comminuted. The splenocyte cells obtained were suspended in approx. 2 ml of Hanks' medium at +4° C., layered on the Ficoll-Uropolin gradient of a density of 1.077, and then centrifugated for 15 min at 3000 rpm at +4° C. After separation from the interphase, the lymphocyte buffy coat was placed in the Hanks' medium at +4° C. and rinsed twice with centrifugation for 7–10 min each time at 1800 rpm. The splenocytes were then suspended in 1 ml of Hanks' medium at such a ratio that it contained $1\times10^6$ cells.

For each test, the percentage of dead cells is determined by mixing a drop of a tested suspension of splenocytes with a drop of ex tempore prepared dyestuff solution containing 4 parts of a 0.2% trypan blue solution and 1 part of a 4.25% NaCl solution. Under the microscope, the percentage of dead splenocytes is determined for each 100 cells. Dead cells are navy blue, while the bright cells are live cells. The presence of more than 10% of dead cells is critical; such a sample has to be eliminated from further use.

All steps carried out with the cells to be tested are performed in a sterile, siliconized laboratory glass apparatus placed in an ice bath.

EXAMPLE 6

In the first test, an effect of the tested reaction products on the number of cells producing hemolytic antibodies (PFC-IgM) was determined. The test was carried out as follows: To 0.5 ml of an 0.5% agarose solution placed in a test tube and kept in a heated water bath at 45° C., 0.1 ml of a 10% suspension of SRBC (prepared as described above) were admixed. Then 0.1 ml of a splenocyte suspension having a density of $1\times10^6$ cells/ml was added, the mixture stirred rapidly and immediately poured out on slides previously covered with agarose. The slides are incubated at 37° C. for two hours. Next, the tested samples are covered with guinea pig complement diluted at a ratio of 1:20 for a further 2 h. After the incubation of the tested samples with the complement, the number of plaque forming cells (PFC) was counted and recalculated for $1\times10^6$ splenocytes. Each test was performed twice.

The strongest amplification of the response to SRBC expressed in terms of increase of the number of splenocytes producing hemolysines IgM (PFC) was observed after administration of the D-11 substance at a dose of 0.1 mg/kg. The amplification was 119%. When the daily dose was increased ten times up to 1 mg/kg, amplification of the response was lowered to 53%.

Reaction product D-12 showed the strongest activity—an increase of 58%—at a dose of 1 mg/kg.

Reaction product $EK_2$-S-11 in this test showed the strongest activity at a dose of 0.1 mg/kg (increase of 65%). At a dose ten times higher, i.e. 1 mg/kg, the increase was slightly lower, i.e. 52%.

Reaction product D-13 tested at a dose of 1 mg/kg caused an increase of 40%. When the dose was increased to 10 mg/kg, i.e. ten times, the response was only a 14% increase.

EXAMPLE 7

An active hemagglutination test was also carried out, determining the level of the anti-SRBC type 19S–7S and 7S the level. In order to determine the 19S–IgM type antibodies level, mouse serum was prepared on the fourth day after immunization with SRBC, while for the determination of 7S–IgG type antibodies level such preparation took place on the tenth day after mice immunization with SRBC, which is related to the day of maximum count of antibodies of a given type in mice immunized with SRBC.

A. Determination of 19S+7S antibodies count.

A sample of blood was centrifuged for 30 min at 3500 rpm. From each sample thus prepared, serum was collected and placed in a heated water bath at a temperature of 56° C. for 30 min in order to deactivate the complement. Next, a number of solutions at several different dilutions of each tested serum was prepared (from 1:1 to 1:4096) employing a microtitrator and U-shaped microplates having a volume of 250 μl each. The diluted sera were incubated for 1 hour at room temperature. A drop of a 1% suspension of SRBC in PBS (prepared as described above) was added to each serum; the mixtures were incubated for a further 2 h at a temperature of 37° C. and then stored at a temperature of +4° C. The results were taken next day. The maximum dilution at which hemagglutination is still caused was considered the anti-body. count. A ring at the bottom of the plate is a sign that hemagglutination occurs. A button-like formation at the bottom of the plate is considered as a negative result—no hemagglutination.

For statistical analysis of the results, the increase of dilution of serum in a tested substance was compared to the one in a control group.

Reaction product D-11 at a dose of 1 mg/kg increased the IgM count 2.57 times. At a ten times higher dose, the stimulation effect in comparison to the control group increased by 3.5 times.

Reaction product D-12 in this test showed a weaker activity. At a dose of 0.1 mg/kg, it increased the IgM count 2 times, and at a dose of 1 mg/kg 1.4 times.

Reaction product $EK_2$-S-11 showed the strongest activity in this test. At a dose of 0.0 mg/kg, it increased the IgM count 4.3 times, and at a dose of 1 mg/kg 3.6 times.

Reaction product D-13 at a dose of 1 mg/kg increased the IgM count 3 times, and at a ten times higher dose 1.5 times.

B. Determination of 75 antibody count

The tested inactivated sera were combined—at a ratio of 1:1—with a 0.1 M solution of 2-mercaptoethanol and the mixtures incubated for 30 min at a temperature of 37° C. 2-Mercaptoethanol destroys immunoglobulins of the 19S–(IgM) type, while immunoglobulins of the 7S-(IgG) type are not susceptible to the action of 2-mercaptoethanol.

After 30 min of incubation, the reduction reaction was stopped by means of cooling down to a temperature of +4° C. for 15 min. Next, a number of dilutions was prepared in a similar manner as described above with respect to determining the 19S-antibody count and combined with a 1% suspension of SRBC; after 2 hours of incubation at 37° C., the samples were stored at a temperature of +4° C. The results were evaluated on the following day, according to the criteria of determining the hemagglutination count described above. Simultaneously, a control test was carried out with a combination of a 1% suspension of SRBC with PBS in a ratio of 1:1.

When the substance D-11 was tested as described above, at a dose of 1 mg/kg it increased the production of antibodies IgG 3.16 times. At a dose of 10 mg/kg, the increase was 2.2 times.

Reaction product D-12 tested at a dose of 0.1 mg/kg and 1 mg/kg respectively stimulated the production of antibodies IgG 1.3 times, and at a dose of 10 mg/kg 1.5 times.

Reaction product $EK_2$-S-11 at a dose of 0.1 mg/kg stimulates the production of IgG 1.9 times, and at a dose of 1 mg/kg 2.89 times (in comparison with the control).

The results of tests A and B obtained for each production lot or for each fraction of the biologically active reaction products synthesized according to the invention and giving the above-mentioned immunological response were subjected to statistical analysis by the T-student method, $\alpha=0.05$. Results obtained for each dose tested were compared with a parallel control test and showed an increase of biological activity.

EXAMPLE 8

The group of biologically active reaction products obtained according to Examples 1 to 5 have also been submitted to the test in which the percentage of splenocytes forming E-rosettes was determined.

250 μl of a 1% suspension of SRBC and 250 μl of cells to be tested at a concentration of $1\times10^6$ cells/ml were added to 550 μl of Hanks' medium. Each such samples was incubated in a heated water bath equipped with a shaker for 15 min at a temperature of 37° C. Then, it was stored at a temperature of +4° C. for a further 20 h. The percentage of splenocytes forming E-rosettes with SRBC was determined after the suspension was colored with 1 to 3 drops of crystal violet.

Each sample was subjected to determination of the percentage of splenocytes three times, counting at each instance 400 splenocytes. A splenocyte surrounded with at least 3 erythrocytes was considered an E-rosette.

For statistical evaluation, the percentage increase of the number of splenocytes with E-rosettes was compared between the substances to be tested and a control group.

In this test, the strongest stimulating effect was shown by the reaction products D-11 (63%) and $EK_2$-S-11 (70%) at a dose of 1 mg/kg. At a dose ten times smaller, i.e. 0.1 mg/kg, the values decreased to 45% and 57% respectively.

Reaction product D-12 at a dose of 1 mg/kg caused an increase of the ability to form E-rosettes of 22% in comparison to the control group. The respective value for a dose ten times smaller, i.e. of 0.1 mg/kg, was 29%.

Reaction product D-13 shows the maximum effect at a dose of 1 mg/kg (58%), while at higher doses the effect is slightly smaller.

Biological activity of synthesized compounds was evaluated according to the following tests:

1. Test for determination of the percentage of splenocytes forming E-rossettes, carried out according to Bach and Dardenne (Cell. Immunol. 3, 1–16, 1972)
2. Test for determination of the number of cells producing hemolytic antibodies of an IgM type, carried out according to the Jerne method, modified by Mishell and Dutton (J. Exp. Med. 126, 423–442, 1967) and
3. Test for determination of a hemagglutination 19S–7S and 7S antibody count, carried out according to Adler's active hemagglutination methods (J. Immunol. 95, 26–38, 39–47, 1965) with the use of microplates (J. Immunopharmacol. 4, 43–52, 1982).

EXAMPLE 9

A rotary evaporator flask placed in a heated water bath was charged with:

1.33 g (0.01M) L-aspartic acid 0.84 g (0.01M) $NahCO_3$ 10.00 g hydrolyzed dextrane of an average molecular weight of 3000 daltons 10.00 ml redistilled water.

The mixture was heated under pressure at a temperature of 70° C. until the solid substances were completely dissolved, expelling by means of distillation during that period approx. 3 ml of water (heating time was approx. 30 min). The flask with the solution was loosely covered, placed in a steam sterilizer and heated under pressure at a temperature of 121° C. for 40 min. After cooling down, the resulting yellow-orange solution was diluted with 15 ml of water, clarified by means of centrifugation and spray dried by air having an inlet temperature of −160° C. and an outlet temperature of +85° C. 10.5 g of a light beige reaction product resulted that was easily soluble in water.

The presence of Amadori rearrangement products in this reaction product was confirmed by a test by the potassium ferricyanide method described by Borsook, Abrams and Lowy, J. Biol. Chem 215, (1955), 111–124 and by chromatographic methods.

Biological tests as described in the preceding Examples confirmed an immunotropic activity of the above product similar to the one exhibited by preparations obtained with simple sugars.

EXAMPLE 10

A conical flask was charged with:

5.0 g hydrolyzed dextrane of an average molecular weight of approx. 5000 daltons 1.1 g L-proline 4.0 ml redistilled water.

The content was dissolved by means of stirring. The uniform mixture thus obtained was placed in a steam sterilizer and heated under pressure at a temperature of 110° C. for 40 min. The resulting transparent orange solution was diluted with 20 ml of redistilled water and clarified by means of centrifugation. The clear solution was spray dried.

5.3 g of a reaction product easily soluble in water was obtained. Immunotropic activity was similar to the one observed in other experiments according to the preceding examples.

EXAMPLE 11

Conventional methods test the biological activity of the compounds in mice, but not in humans. For this reason, new bio-assays have been introduced, which measure the amounts and activity of cytokines released from the human peripheral blood leukocytes (PBL) treated with the reaction products according to the Examples 1 to 5, 9 and 10. The cytokines are the hormone-like proteins that play an important role in practically all of the immunological reactions, as well as in the regulatory processes responsible for the maintenance of homeostasis.

Cytotoxicity assays.

Cytotoxicity of the reaction products was determined in human lung adenocarcinoma cell line A549 (included in the American Type Culture Collection—ATCC CCL 185). The cell monolayers were trypsinized, suspensions of $2 \times 10^5$ cells/ml in Dulbecco's-modified Eagle's minimum essential medium (DMEM) plus 10% calf serum (CS) were mixed with various doses of the drugs, seeded in the plastic microplates, and incubated for 48 h at 37° C. $CD_{50}$ was the minimal concentration of the compound which caused approximately 50% destruction of the cell culture as measured by staining with 0.015% solution of neutral red in DMEM.

Cytokine induction.

Buffy coats from healthy blood donors were obtained from the regional transfusion center. The erythrocytes were lysed by $NH_4Cl$ treatment according to Cantell et al. (Cantell, K., Hirvonen, S., Kauppinen, H. L.: Production and Partial Purification of Human Immune Interferon. Meth. Enzymol., 119, 54, 1986). The leukocytes from a single donor containing approximately $8 \times 10^6$ leukocytes/ml in RPMI 1640 medium supplemented with 10% fetal calf serum (FCS), L-glutamine, and antibiotics were used. All lots of FCS were pretested. Only non-mitogenic FCS for PBL cultures was used. The cytokine inducers were added to 1 ml volumes of the cultures. The reference cytokine inducers were phytohemagglutinin (PHA) (Pharmacia Fine Chemicals, Sweden) and LPS from *E. coli* 0111:B4 (Difco Laboratories). The induced cultures of PBL were incubated in an atmosphere of 5% $CO_2$ in air at 37° C. for 20 h and centrifuged. Supernatants were stored at 4° C. and assayed for TNF and IFN activity within one week.

Interferon (IFN) assay.

The confluent monolayer of A549 cells was prepared in the microplates in DMEM with 10% CS, L-glutamine, and antibiotics (100 units/ml penicillin and 100 µg/ml streptomycin). IFN samples diluted in plates were added to the cell monolayer and incubated at 37° C. for 20 h in 5% $CO_2$ in air. The cells were then washed and challenged with encephalomyocarditis virus (EMCV). The titer of IFN was defined as the dilution of IFN sample that reduced the virus cytopathogenic effect by 50% after 48 h of incubation. The MTT (3-[4,5-dimethylthiazol-2-yl]-2,5-diphenyltetranolium bromide) method (Hansen, M. B., Nielsen, S. E., and Berg, K.: Re-examination and Further Development of a Precise and Rapid Dye Method for Measuring Cell Growth/ Cell Kill. J. Immuno. Meth., 1989, 119, 203–210) to measure the cell kill in the ELISA scanner was also used. Laboratory standards of IFNs were included in all assays: Recombinant human IFN-γ (Genentech Inc., USA, specific activity $2 \times 10^8$ units/mg), the natural human leukocyte IFA-α ($3 \times 10^6$ IU/ml) and IFN-γ ($2 \times 10^6$ IU/ml) obtained from Dr. K. Cantell, Helsinki, Finland.

Tumor Necrosis Factor (TNF) assay.

The cytotoxic activity of TNF was measured in L929 cells according to Flick and Gifford (Flick, D. A., Gifford, G. E.: Comparison of in Vitro Cell Cytoxic Assays for Tumor Necrosis Factor. J. Immunol. Meth., 68, 167, 1984).

The sample and actinomycin D solution were added to monolayer cultures of the cells. After incubation at 37° C. for 20 h, the cultures were stained with crystal violet and toxic effects were determined. The amount causing approximately 50% destruction of the cell cultures was defined as one unit of TNF activity. Comparison with a preparation of TNF-α (Genentech Inc., USA) showed that 1 unit in our assays was equal to 100–200 pg/ml TNF.

Cytokine neutralization assays.

The antisera used were: rabbit anti-human TNF-α, lot 2958-40 and rabbit anti-human IFN-γ, lot 2891-56 (Genentech Inc., USA), sheep anti-human IFN-α,β, and sheep anti-human IFN-γ (obtained from Dr. K. Cantell, Finland). The cytokine preparations were treated with the sera diluted 1:200 in culture medium and incubated for one hour at room temperature. Then, the residual IFN or TNF activities were determined as described.

Five different batches ($L_1$ to $L_5$) of PBL prepared from the blood of healthy blood donors were used. The optimal PBL concentration for the assays was found to be $8 \times 10^6$ cells per one ml of medium (RPMI 1640 supplemented with 10% fetal calf serum and antibiotics).

Incubation of human PBL with the new reaction products I–XI (Table 1) resulted in IFN and TNF synthesis. The observed responses were dose related in the range of 3–100 µg/ml of the compounds (Table 2). The compounds used in the indicated concentrations were non-cytotoxic. In all of the bioassays, negative and positive controls were included. The negative controls measured the amounts of the cytokines (IFN and TNF) produced spontaneously without the addition of any exogenous stimulants. The positive controls indicated the amounts of the cytokine produced in response to a known reference inducer; in our case this was phytohemagglutinin (PHA, Pharmacia, Sweden, 10 µg per ml).

It should be pointed out that the cytokine induction in human PBL cultures obtained from different individuals usually gives considerable variation of the results. The phenomenon may be explained in terms of genetic differentiation of human population. Furthermore, PBL cultures often produce IFN and TNF spontaneously.

In other words, high responders and low responders or even non-responders are commonly observed among the healthy donors of PBL.

Despite the presented limitations, the results of the bioassays showed that PBL ($L_1$ to $L_5$) treated with the reaction products (I–XI) produced IFN and/or TNF that could be measured quantitatively.

In the case of $L_1$ which contained leukocytes of the high responder, the reaction product II (containing L-form of aspartic acid) was found to be considerably more active as a cytokine inducer than the reaction product III (containing the D-form of aspartic acid which also is more expensive by two orders of magnitude). The observation is significant because mainly L-forms of the amino-acids are recognized by cells as natural substrates in biochemical reactions.

Furthermore, for the expression of biological activity of the reaction products, the amino-acid part of the molecule is much more important than the form of sugar. Instead of single sugars,—preferably low molecular weight, especially of less than 1000 daltons—polysaccharides (such as dextranes, reaction products X–XI) can be used and they react similarly.

And vise versa, polysaccharides containing the amino-acid residues may have biological activity, and this activity is retained when they are decomposed to oligosaccharides with the bound amino-acid (data not shown).

Similar results may also be observed if a short peptide is taken instead of a single amino-acid and is used to stimulate the leukocytes to produce cytokines (data not shown).

Seven reference batches of the unfactionated TTP assayed in over 100 PBL cultures from different donors produced from 10 to 1,000 units of IFN per ml, and from 9 to 750 units of TNF per ml. The fraction $EK_2$–S prepared from a mixture corresponding to the contents of natural peat extract (Example 5) has been assayed in eight PBL cultures from eight different blood donors. It was found to be the most active preparation in inducing both IFN and TNF (data not shown).

Possible applications of the reaction products are as immuno-modulators and such activity was clinically useful. Tissue regeneration is another proven activity. Anti-cancer activity probably connected with the presence of the induced interferon and tumor necrosis factor was also observed. Anti-viral activity was also noted.

The main use of the above reaction products involves oral administration, but parenteral treatment is also possible, as is, topical application. The products appear relatively stable.

TABLE 1

List of Reaction products

| No. | Substrates |
| --- | --- |
| I (D-10) | L-glutamic acid, glucose, galactose |
| II (D-11) | L-aspartic acid, glucose, galactose |
| III (D-13) | D-aspartic acid, glucose, galactose |
| IV (D-12) | L-serine, glucose, galactose |
| V | $EK_2$-S (fractions 11–13) |
| VI | $EK_2$-S (fractions 6–7) |
| VII | $EK_2$-S (fractions 8–10) |
| VIII | $EK_2$-S (fractions 28–34) |
| IX | L-proline, glucose |
| X | L-aspartic acid + dextrane (variety 1) |
| XI | L-aspartic acid + dextrane (variety 2) |

EXAMPLE 12

Pharmaceutical formulations containing as an active ingredient the reaction products according to Examples 1 to 5, 9 and 10, were prepared using the following reaction products:

A. Tablets/Granules:

5.0 g of the reaction product obtained according to Example 1 or 10 (active substance), 444.0 g of pharmaceutically acceptable lactose 1.0 g of lubricant (e.g. MYVATEX®, trademark of Eastman Kodak)

The ingredients were mixed and granulated with 30% aqueous ethanol in a conventional way, then dried at 40° C. The granules were used to prepare capsules, each containing approx. 450 mg of granules, i.e. 5 mg of the active substance. Alternatively, the granules were used to form tablets, each weighing approx. 450 mg and containing 5 mg of the active substance.

B. In the same conventional manner, the active substances obtained according to the preceding examples 1 to 5, 9 and 10 were formulated into other pharmaceutical formulations using suitable carriers.

TABLE 2

Biological Activity of the Reaction Products I-XI in Human PBL

| | Dose | IFN Units/ml | | | | | INF units/ml | | | | |
| --- | --- | --- | --- | --- | --- | --- | --- | --- | --- | --- | --- |
| | µg/ml | $L_1$ | $L_2$ | L | L | L | L | L | L | L | L |
| Control | — | 10 | <10 | <10 | 20 | <10 | 80 | 9 | 27 | 27 | <9 |
| PHA | 10 | 100 | 30 | 30 | 60 | 100 | 250 | 80 | 250 | 250 | 250 |
| I | 100 | 100 | <10 | <10 | 20 | — | 250 | 9 | 9 | 160 | — |
| | 30 | — | — | — | 30 | — | — | — | — | 500 | — |
| | 10 | 30 | <10 | <10 | 30 | — | 80 | 9 | 18 | 160 | — |
| | 3 | — | — | — | 10 | — | — | — | — | 160 | — |
| II | 100 | 100 | 10 | <10 | 10 | <10 | 250 | 18 | 18 | 250 | <9 |
| | 30 | — | — | — | 10 | <10 | — | — | — | 250 | <9 |
| | 10 | 1000 | 10 | 30 | 10 | 10 | 250 | 50 | 27 | 250 | <9 |
| | 3 | — | — | — | 10 | <10 | — | — | — | 160 | <9 |
| III | 100 | <10 | <10 | 10 | 10 | <10 | 250 | 9 | 18 | 250 | <9 |
| | 30 | — | — | — | 30 | <10 | — | — | — | 250 | <9 |
| | 10 | <10 | <10 | <10 | 10 | <10 | 80 | 27 | 18 | 250 | <9 |
| | 3 | — | — | — | 10 | <10 | — | — | — | 80 | <9 |
| IV | 100 | <10 | 10 | 10 | 20 | <10 | 80 | 60 | 9 | 160 | <9 |
| | 30 | — | — | — | 20 | <10 | — | — | — | 27 | <9 |

TABLE 2-continued

Biological Activity of the Reaction Products I-XI in Human PBL

| | Dose μg/ml | IFN Units/ml | | | | | INF units/ml | | | | |
|---|---|---|---|---|---|---|---|---|---|---|---|
| | | $L_1$ | $L_2$ | L | L | L | L | L | L | L | L |
| | 10 | <10 | 30 | <10 | 20 | <10 | 80 | 50 | 18 | 80 | <9 |
| | 3 | — | — | — | 20 | <10 | — | — | — | 80 | <9 |
| V | 100 | 30 | <10 | <10 | 60 | — | 80 | 50 | 18 | 250 | — |
| | 30 | — | — | — | 60 | — | — | — | — | 80 | — |
| | 10 | <10 | <10 | <10 | 10 | — | 80 | 27 | 9 | 80 | — |
| | 3 | — | — | — | 10 | — | — | — | — | 80 | — |
| VI | 100 | <10 | <10 | <10 | 20 | — | 80 | 27 | 18 | 80 | — |
| | 30 | — | — | — | 10 | — | — | — | — | 80 | — |
| | 10 | 10 | <10 | <10 | 20 | — | 50 | 27 | 18 | 160 | — |
| | 3 | — | — | — | 10 | — | — | — | — | 250 | — |
| VII | 100 | <10 | <10 | <10 | — | — | 80 | 27 | 27 | — | — |
| | 30 | — | — | — | — | — | — | — | — | — | — |
| | 10 | 10 | <10 | <10 | — | — | 80 | 27 | 27 | — | — |
| | 3 | — | — | — | — | — | — | — | — | — | — |
| VIII | 100 | <10 | <10 | <10 | — | — | 80 | 160 | 27 | — | — |
| | 30 | — | — | — | — | — | — | — | — | — | — |
| | 10 | <10 | <10 | <10 | — | — | 750 | 80 | 27 | — | — |
| | 3 | — | — | — | — | — | — | — | — | — | — |
| IX | 100 | 10 | <10 | <10 | 10 | — | 27 | 27 | 18 | 80 | — |
| | 30 | — | — | — | 20 | — | — | — | — | 80 | — |
| | 10 | 100 | 30 | <10 | 20 | — | 80 | 27 | 18 | 80 | — |
| | 3 | — | — | — | 10 | — | — | — | — | 50 | — |
| X | 100 | 100 | <10 | 20 | 20 | — | 27 | 27 | 18 | 250 | — |
| | 30 | — | — | — | 30 | — | — | — | — | 80 | — |
| | 10 | <10 | 10 | <10 | 30 | — | 18 | 50 | 27 | 50 | — |
| | 3 | — | — | — | 30 | — | — | — | — | 250 | — |
| XI | 100 | <10 | 10 | <10 | 30 | — | 18 | 27 | 27 | 50 | — |
| | 30 | — | — | — | 10 | — | — | — | — | 250 | — |
| | 10 | <10 | 30 | <10 | 10 | — | 18 | 80 | 80 | 80 | — |
| | 3 | — | — | — | 20 | — | — | — | — | 750 | — |

EXAMPLE 13

The active substances obtained according to preceding Examples 1 to 5, 9 and 10 were used as a beneficial additive to cosmetic preparations intended for everyday hair and body care, the content of the substances being within a range of 0.01–10% by weight, depending on the type of the preparation, the method of application and the frequency of use intended for the particular preparation.

We claim:

1. A composition comprising a mixture of at least two different Amadori rearrangement compounds of the general formula $R_1$—NH—$R_2$, wherein $R_1$ is a 1-deoxy-2-ketose radical derived from a simple sugar, oligo- or polysaccharide, and $R_2$ is an amino acid or peptide radical, the mixture being capable of stimulating an immune system by inducing cytokine formation.

2. The composition of claim 1, wherein at least one of the radicals is derived from a compound selected from the group consisting of an oligo- or polysaccharide having a molecular weight of 5000 daltons or less, and a peptide having a molecular weight of less than 1000 daltons.

3. The composition of claim 1, wherein the mixture further comprises inorganic trace elements.

4. The composition of claim 1, wherein the simple sugar is selected from the group consisting of glucose, xylose, galactose, rhamnose, fructose, mannose, 2-deoxy-glucose, 6-deoxy-glucose, glucosamine, and galactosamine.

5. The composition of claim 1, wherein the amino acid radical is selected from the group consisting of serine, glycine, proline, histidine, arginine, alanine, aspartic acid, glutamic acid, phenylalanine, threonine, cysteine, cyrstine, glutamine, valine, asparagine, methionine, tyrosine, hydroxyproline, lysine, tryptophane, isoleucine, and leucine.

6. The composition of claim 1, further comprising at least one substance selected from the group consisting of a pharmaceutically-acceptable carrier, a cosmetically acceptable carrier, an adjuvant, and a lubricant, a weight ratio of the at least one Amadori rearrangement compound to the at least one substance being between 1:1 to 1:100.

7. The composition of claim 6, wherein the weight ratio ranges from 1:8 to 1:20.

8. The composition of claim 6, wherein the weight ratio is about 1:9.

9. The composition of claim 6, comprising a lubricant present in admixture with lactose, a weight ratio of lactose to the lubricant being between 20:1 and 100:1.

10. The composition of claim 9, wherein the weight ratio of lactose to the lubricant is about 50:1.

11. A cosmetic preparation comprising at least one cosmetically-acceptable carrier or additive and at least one Amadori rearrangement compound of the general formula $R_1$—NH—$R_2$, wherein $R_1$ is a 1-deoxy-2-ketose radical derived from a simple sugar, oligo- or polysaccharide, and $R_2$ is an amino acid or peptide radical.

12. The cosmetic preparation of claim 11, further comprising at least one other Amadori rearrangement compounds of the general formula $R_1$—NH—$R_2$, wherein $R_1$ is a 1-deoxy-2-ketose radical derived from a simple sugar, oligo- or polysaccharide, and $R_2$ is an amino acid or peptide radical, the mixture being capable of stimulating an immune system by inducing cytokine formation.

13. The cosmetic preparation of claim 12, wherein at least one of the radicals is derived from a compound selected from the group consisting of an oligo- or polysaccharide having a molecular weight of 5000 daltons or less, and a peptide having a molecular weight of less than 1000 daltons.

14. The cosmetic preparation of claim 12, further comprising inorganic trace elements.

15. The cosmetic preparation of claim 12, wherein the simple sugar is selected from the group consisting of glucose, xylose, galactose, rhamnose, fructose, mannose, 2-deoxy-glucose, 6-deoxy-glucose, glucosamine, and galactosamine.

16. The cosmetic preparation of claim 12, wherein the amino acid radical is selected from the group consisting of serine, glycine, proline, histidine, arginine, alanine, aspartic acid, glutamic acid, phenylalanine, threonine, cysteine, cystine, glutamine, valine asparagine, methionine, tyrosine, hydroxyproline, lysine, tryptophane, isoleucine, and leucine.

17. The cosmetic preparation of claim 12, further comprising at least one substance selected from the group consisting of a pharmaceutically-acceptable carrier, a cosmetically acceptable carrier, an adjuvant, and a lubricant, a weight ratio of the at least one Amadori rearrangement compound to the at least one substance being between 1:1 to 1:100.

18. The cosmetic preparation of claim 17, wherein the weight ratio ranges from 1:8 to 1:20.

19. The cosmetic preparation of claim 17, wherein the weight ratio is about 1:9.

20. The cosmetic preparation of claim 17, comprising a lubricant present in admixture with lactose, a weight ratio of lactose to the lubricant being between 20:1 and 100:1.

21. The cosmetic preparation of claim 20, wherein the weight ratio of lactose to the lubricant is about 50:1.

22. The cosmetic preparation of claim 11, wherein the at least one Amadori rearrangement compound is present in an amount of 0.01–10% by weight.

23. A cosmetic preparation according to claim 22, wherein the at least one Amadori rearrangement compound is represent in an amount of 0.01–1% by weight.

24. A cosmetic preparation according to claim 22, wherein the at least one Amadori rearrangement compound is present in an amount of 0.05–0.10% by weight.

25. A process for the manufacture of a mixture of at least two different Amadori rearrangement compounds as defined in claim 1, the process comprising the steps of:
   a) reacting at least one amino acid or peptide with at least one simple sugar, oligo- or polysaccharide in the presence of water as a solvent at a temperature of about 70°–121° C.;
   b) continuing said reaction to allow the resulting products to undergo Amadori rearrangement while simultaneously or subsequently removing the aqueous solvent, until the reaction mixture turns light orange brown in color and biological activity and ferricyanide reducing capacity can be detected in samples taken from the mixture;
   c) stopping the Amadori rearrangement before decomposition yields compounds that have lost their biological activity; and thereafter
   d) with drying the resulting mixture containing said at least two different Amadori rearrangement compounds or further subjecting that mixture to a purification by column chromatography and selectively collecting biologically active fractions that cause reduction of potassium ferricyanide.

26. The process of claim 25, wherein said reaction is carried out for about 30 to 120 minutes.

27. The process of claim 25, wherein the reaction is carried out in the presence of inorganic trace elements.

28. The process of claim 27, wherein the reaction is carried out under pressure.

29. The process of claim 27, wherein the reaction is carried out in the presence of a lower alcohol.

30. The process of claim 28, wherein the reaction is carried out in the presence of a lower alcohol.

31. The process of claim 25, wherein the molar ratio of sugars, oligo- or polysaccharides to the amino acids and peptides is between 2:1 and 1:1.

32. The process of claim 25, wherein the mixture comprises at least one compound selected from the group consisting of an oligo- or polysaccharide having a molecular weight of 5000 daltons or less, and a peptide having a molecular weight of less than 1000 daltons.

33. The process of claim 25, wherein at least one amino acid has two carboxyl groups and the reaction is carried out in the presence of a buffer salt in a molar ratio with the amino acid of 1:1.

34. The process of claim 33, wherein the buffer salt is sodium bicarbonate.

35. The process of claim 25 wherein the reaction is carried out in a concentrated aqueous solution of about 0.67 to about 2.75 pbw of solids per 1 pbw of aqueous solvent.

36. The process of claim 25, further comprising the step of adding at least one pharmaceutically or cosmetically acceptable carrier or additive to the mixture of the Amadori rearrangement compounds obtained by step (d).

37. A method of cytokine induction by polyclonal activation of mammalian cells, the method comprising the step of administering to mammalian cells a preparation comprising a cytokine induction effective amount of at least one biologically active Amadori rearrangement compound of the general formula $R_1$—NH—$R_2$, wherein $R_1$ is a 1-deoxy-2-ketose radical derived from a simple sugar, oligo- or polysaccharide and $R_2$ is an amino acid or peptide radical.

38. The method of claim 37, wherein the preparation comprises at least two different Amadori rearrangement compounds.

39. The method of claim 38, wherein at least one of the radicals is derived from a compound selected from the group consisting of an oligo- or polysaccharide having a molecular weight of 5000 daltons or less, and a peptide having a molecular weight of 1000 daltons or less.

40. The method of claim 38, wherein the mixture further comprises inorganic trace elements.

41. The method of claim 38, wherein the simple sugar is selected from the group consisting of glucose, xylose, galactose, rhamnose, fructose, mannose, 2-deoxy-glucose, 6-deoxy-glucose, glucosamine, and galactosamine.

42. The method of claim 38, wherein the amino acid radical is selected from the group consisting of serine, glycine, proline, histidine, arginine, alanine, aspartic acid, glutamic acid, phenylalanine, threonine, cysteine, cystine, glutamine, valine, asparagine, methionine, tyrosine, hydroxyproline, lysine, tryptophane, isoleucine, and leucine.

43. The method of claim 38, wherein the preparation further comprises at least one substance selected from the group consisting of a pharmaceutically-acceptable carrier, a cosmetically acceptable carrier, an adjuvant, and a lubricant, a weight ratio of the at least one Amadori rearrangement compound to the at least one substance being between 1:1 to 1:100.

44. The method of claim 43, wherein the weight ratio ranges from 1:8 to 1:20.

45. The method of claim 43, wherein the weight ratio is about 1:9.

46. The method of claim 43, wherein the preparation comprises a lubricant present in admixture with lactose, a weight ratio of lactose to the lubricant being between 20:1 and 100:1.

47. The method of claim 46, wherein the weight ratio of lactose to the lubricant is about 50:1.

48. The method of claim 46, wherein the Amadori rearrangement compound is administered as a prophylactic or therapeutic treatment to a human or animal body in need of such treatment.

49. The method of claim 39, wherein the at least one Amadori rearrangement compound is administered as a prophylactic or therapeutic treatment to a human or animal body in need of such treatment.

* * * * *